US00PP21446P2

(12) United States Plant Patent
van Kleinwee

(10) Patent No.: US PP21,446 P2
(45) Date of Patent: Nov. 2, 2010

(54) ***ARGYRANTHEMUM FRUTESCENS* PLANT NAMED 'ARGYBIDARO'**

(50) Latin Name: *Argyranthemum frutescens*
Varietal Denomination: Argybidaro

(75) Inventor: Theodorus Cornelis Maria van Kleinwee, Zwaag (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/586,816

(22) Filed: Sep. 29, 2009

(51) Int. Cl.
*A01H 5/00* (2006.01)

(52) U.S. Cl. ..... Plt./406

(58) Field of Classification Search ..... Plt./263, Plt./406
See application file for complete search history.

*Primary Examiner*—Susan B McCormick Ewoldt
(74) *Attorney, Agent, or Firm*—S. Matthew Edwards

(57) ABSTRACT

A new and distinct cultivar of *Argyranthemum frutescens* plant named 'Argybidaro' characterized by its rather vigorous round plant habit with dark green foliage, and its early, rich and long flowering with pink flowers with a contasting dark red center and a semi double flowering habit.

1 Drawing Sheet

Latin name of the genus and species of the plant claimed: *Argyranthemum frutescens.*

Varietal denomination: 'Argybidaro'.

BACKGROUND OF THE NEW PLANT

The present invention relates to a new and distinct cultivar of Marguerite Daisy plant, botanically known as *Argyranthemum frutescens* and hereinafter referred to by the cultivar name 'Argybidaro'.

The new cultivar is a product of a planned breeding program conducted in Enkhuizen, Netherlands.

The new *Argyranthemum* originates from an open pollination conducted in Enkhuizen, Netherlands in 2004 of a proprietary selection of *Argyranthemum frutescens* identified as code number 'D0260-1,' not patented, as the female, or seed, parent with pollen of unknown *Argyranthemum frutescens* plants as the male, or pollen, parent.

The cultivar 'Argybidaro' was discovered and selected as a single plant within the progeny of the stated open pollination in a controlled environment in Enkhuizen, Netherlands, in August 2005. Asexual reproduction of the new *Argyranthemum* by terminal cuttings in a controlled environment in Enkhuizen, Netherlands since August 2005, has shown that the unique features of this new *Argyranthemum* are stable and reproduced true to type in successive generations.

A Plant Breeder's Right for this cultivar was applied for in the European Union in December 2008. 'Argybidaro' has not been made publicly available more than one year prior to the filing of this application.

SUMMARY OF THE INVENTION

The new *Argyranthemum* has not been observed under all possible environmental conditions. The phenotype may vary somewhat with variations in environment such as temperature and light intensity without, however, any variance in genotype.

The following characteristics have been repeatedly observed and are determined to be basic characteristics of 'Argybidaro' and distinguish to new *Argyranthemum* as a new and distinct cultivar:

1. Vigorous round plant habit.
2. Early flowering habit.

3. Freely flowering habit with numerous inflorescences per plant.
4. Dark green foliage.
5. Semi double flowers.
6. Pink flowers with a contrasting dark red center.

Plants of the new *Argyranthemum* differ from plants of the female parent in the following characteristics:

'Argybidaro' has a dark red center while the female parent has a yellow center in the flower.

'Argybidaro' has a strongly fading flower color while the female parent is rather stable in its pink color.

'Argybidaro' has very long peduncles while the female parent has medium length peduncles.

Difference of plants of the new *Argyranthemum* from plants of the male parent is unknown, as the male parent is unknown.

TABLE 1

DIFFERENCES BETWEEN THE NEW CULTIVAR 'ARGYBIDARO' AND A SIMILAR CULTIVAR

| | 'ARGYBIDARO' | 'Argyros (U.S. Plant Pat. No. 20,015) |
|---|---|---|
| Plant vigor | Strong | Medium |
| Branching | Rather good | Very good |
| Flower color | Pink with dark center | Pink with yellow center |

DESCRIPTION OF THE PHOTOGRAPHS

The accompanying color photographs illustrate the overall appearance of the new cultivar, showing the colors as true as it is reasonably possible to obtain in colored reproductions of this type. Colors in the photograph may differ slightly from the color values cited in the detailed botanical description which accurately describe the colors of the new *Argyranthemum.*

DESCRIPTION OF THE NEW CULTIVAR

The aforementioned photographs, following detailed observations and averaged measurements describe plants of this new Marguerite Daisy plant. The data were collected from plants from asexual reproductions carried out in Enkhuizen, Netherlands. The plant history was taken on plants of 13 weeks old, grown in the greenhouse in Enkhuizen, Netherlands, with day temperatures ranging from 20 to 35° C., and night temperatures ranging from 10 to 20° C.

Color references are primarily to The R.H.S. Colour Chart of The Royal Horticultural Society, 2001 Edition, except where general terms of ordinary dictionary significance are used.

The plant:

*Classification.*—Botanical: *Argyranthemum frutescens.*

Parentage:

*Female parent.*—Proprietary selection of *Argyranthemum frutescens* identified as number 'D-0260-1' (not patented).

*Male parent.*—Unidentified plant of *Argyranthemum frutescens.*

Propagation:

*Type of cuttings.*—Terminal cuttings.

*Time to intiate roots.*—7-10 days at air temperature of 21° C.

*Time to develop roots.*—7-14 days at air temperature of 18° C.

*Root description.*—Fibrous, relatively fine, white in color.

*Rooting description.*—Freely branching, dense.

Plant description:

*Growth habit.*—Round shape.

*Plant height.*—About 17 cm.

*Vigor.*—Very vigorous.

*Spreading area.*—About 25 cm.

*Strength.*—Very strong.

*Branching character.*—Rather freely branching, plants do not require pinching.

*Crop time.*—About 9 weeks are required to produce a finished flowering plant in a 10.5 cm container from a well developed cutting.

Lateral branch description:

*Length.*—14-18 cm.

*Diameter.*—3-4 mm.

*Shape.*—Round, slightly grooved.

*Anthocyanin pigmentation.*—Present.

*Texture.*—Smooth, glabrous.

*Length of internode.*—4-5 cm.

*Pubescence.*—Absent.

*Color.*—147D with anthocyanin spots N187A.

The foliage:

*Arrangement.*—Alternate, simple.

*Shape of leaf.*—Bipinnatisect.

*Leaf apex.*—Broadly acute.

*Leaf base.*—Attenuate, clasping.

*Margin.*—Deeply dissected, laciniate.

*Texture.*—Smooth, glabrous.

*Length.*—3-6 cm.

*Width.*—2-4 cm.

*Depth of incision.*—Laciniate.

*Color.*—Upper side: 137B. Lower side: 138A.

*Pubescence.*—Absent.

*Petiole.*—Length: About 1.5-2.5 cm. Diameter: About 2 mm. Texture: Smooth, glabrous. Color: 138A.

*Venation.*—Shape: Pinnate. Color: 138B.

The inflorescence:

*Appearance.*—Daisy-type inflorescences with ligulate ray florets and well developed, trumpet shaped disc florets. Disc and ray florets develop acropetally on a capitulum. Inflorescences held upright and outwardly on terminal and axillary peduncles. Inflorescences positioned perpendicular to the peduncles. Inflorescences persistent.

*Flowering response.*—Under natural conditions, plants flower continuously from spring to early fall. Inflorescence longevity: 10 days. Quantity of inflorescences: Freely flowering, about 20 open inflorescences and 30 inflorescence buds per plant.

The flower bud:

*Peduncle.*—Length: 10-12 cm. Diameter: 2 mm. Strength: Strong. Aspect: Upright to slightly outward. Texture: Smooth, glabrous. Color: 137C.

*Inflorescence bud.*—Height: 6 mm. Diameter: 8 mm, just before moment of opening of flower. Shape: Ovoid. Color: 137C near peduncle to 70A near top.

The inflorescence:

*Size.*—Diameter: 4 cm. Depth: About 10 mm.

*Disc diameter.*—About 13 mm.

*Receptacle.*—Height: About 6 mm. Diameter: About 10 mm.

*Involucre.*—Number of bracts: 20-25 bracts, organized in whorls. Shape: Elliptic. Apex: Broad. Base: Truncate. Texture: Smooth glabrous. Margin: Entire. Length: 2-3 mm. Width: 1 mm. Color upper and lower side: 148C, 137C towards peduncle.

*Fragrance.*—Absent.

Ray florets:

*Quantity per inflorescence.*—About 14, one whorl.

*Shape.*—Ligulate.

*Apex.*—Tridentate.

*Base.*—Attenuate.

*Margin.*—Entire.

*Color upper surface.*—70A in young flower, fading to 70D in old flower.

*Color lower surface.*—70A in young flower, fading to 70B in old flower.

*Length.*—About 1.3 cm.

*Width.*—0.4 cm.

*Texture.*—Smooth, glabrous; longitudinally ridged.

Disc florets:

*Arrangement.*—Massed at the center of the inflorescence.

*Shape.*—Trumpet shaped, elongated, five-pointed.

*Color.*—Immature: 58A. Mature: N155B with yellow tips 17A.

*Diameter.*—Apex: 4 mm. Base: <1 mm.

*Length.*—0.6 cm.

*Quantity per inflorescence.*—Approximately 150.

*Androecium.*—Presence: Absent on ray florets; present on disk florets. Stamen quantity per floret: 5. Anther length: About 1 mm. Anther shape: Oval. Anther color: 14A. Pollen color: 14A. Amount of pollen: Rather abundant.

*Gynoecium.*—Presence: Present on ray and disc florets. Number of pistils per floret: 1. Pistil length: Approximately 3 mm. Style color: Lighter than 149D. Style length: Approximately 1 mm. Stigma color: 14A. Stigma shape: Bilobed. Ovary color: 157D.

Seed and fruit development: Seed and fruit development has not been observed.

Disease resistance: No disease/pest resistance has been observed to date.

Temperature/weather tolerance: Plants of the new *Argyanthemum* have been observed to be tolerant to rain, wind and to temperatures from 0° C. to 36° C.

What is claimed is:

1. A new and distinct variety of *Argyranthemum frutescens* plant, named 'Argybidaro,' as substantially illustrated and described herein.

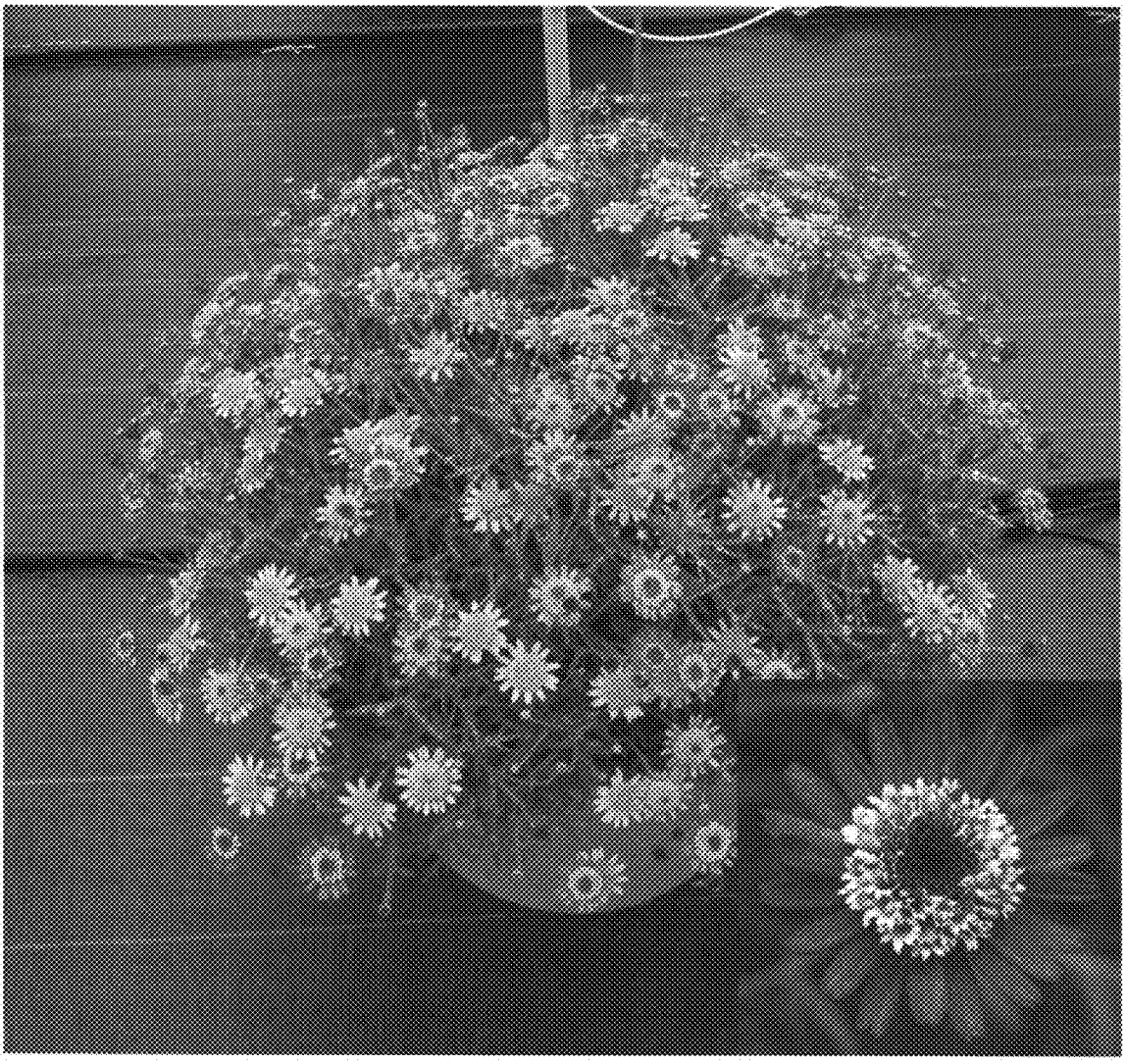

* * * * *